(12) United States Patent
Hingston et al.

(10) Patent No.: US 9,907,644 B2
(45) Date of Patent: Mar. 6, 2018

(54) PARTIALLY COATED STENTS

(71) Applicant: BOSTON SCIENTIFIC SCIMED, INC., Maple Grove, MN (US)

(72) Inventors: John Allen Hingston, Framingham, MA (US); Matthew B. Hollyer, Williamstown, VT (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/612,981

(22) Filed: Jun. 2, 2017

(65) Prior Publication Data

US 2017/0265981 A1    Sep. 21, 2017

Related U.S. Application Data

(63) Continuation of application No. 14/680,593, filed on Apr. 7, 2015.

(Continued)

(51) Int. Cl.
*A61F 2/90* (2013.01)
*A61F 2/07* (2013.01)
(Continued)

(52) U.S. Cl.
CPC ............ *A61F 2/07* (2013.01); *A61F 2/0077* (2013.01); *A61F 2/04* (2013.01); *A61F 2/86* (2013.01);
(Continued)

(58) Field of Classification Search
CPC ........ A61F 2/07; A61F 2002/072; A61F 2/86; A61F 2/90; A61F 2250/0031
See application file for complete search history.

(56) References Cited

U.S. PATENT DOCUMENTS 6,245,099 B1    6/2001    Edwin et al.
6,375,787 B1    4/2002    Lukic
(Continued)

FOREIGN PATENT DOCUMENTS

JP    2013505108 A    2/2013
JP    5260964 B2    8/2013
(Continued)

*Primary Examiner* — David Isabella
*Assistant Examiner* — Suba Ganesan
(74) *Attorney, Agent, or Firm* — Seager, Tufte & Wickhem, LLP

(57) ABSTRACT

A medical product comprises a biodegradable filament and a non-biodegradeable coating. The biodegradable filament forms a stent body having a first end portion, a middle portion, and a second end portion opposite the first end portion. The middle portion extends between the first and second end portions. The non-biodegradeable coating encapsulates the at least one biodegradable filament along the middle portion of the stent body. The non-biodegradeable coating forms a barrier such that the non-biodegradeable coating prevents degradation of the at least one biodegradable filament along the middle portion. The first and second end portions are uncoated. After implantation, the end portions of the stent may biodegrade. The middle portion will not biodegrade due to its encapsulation by the non-biodegradeable coating.

20 Claims, 3 Drawing Sheets

Related U.S. Application Data

(60) Provisional application No. 61/976,764, filed on Apr. 8, 2014.

(51) Int. Cl.

| | | |
|---|---|---|
| *A61F 2/95* | (2013.01) | |
| *A61L 31/10* | (2006.01) | |
| *A61L 31/14* | (2006.01) | |
| *A61L 31/04* | (2006.01) | |
| *A61F 2/86* | (2013.01) | |
| *A61F 2/04* | (2013.01) | |
| *A61F 2/00* | (2006.01) | |

(52) U.S. Cl.
CPC .................. *A61F 2/90* (2013.01); *A61F 2/95* (2013.01); *A61L 31/048* (2013.01); *A61L 31/10* (2013.01); *A61L 31/148* (2013.01); *A61F 2002/009* (2013.01); *A61F 2002/044* (2013.01); *A61F 2002/072* (2013.01); *A61F 2002/9528* (2013.01); *A61F 2210/0004* (2013.01); *A61F 2250/003* (2013.01); *A61F 2250/0031* (2013.01); *A61F 2250/0039* (2013.01); *A61F 2250/0041* (2013.01); *A61F 2250/0059* (2013.01); *A61L 2420/00* (2013.01)

(56) References Cited

U.S. PATENT DOCUMENTS

| | | |
|---|---|---|
| 6,451,047 B2 | 9/2002 | McCrea et al. |
| 6,808,533 B1 | 10/2004 | Goodwin et al. |
| 7,147,659 B2 | 12/2006 | Jones |
| 7,354,449 B2 | 4/2008 | Goodwin et al. |
| 7,651,527 B2 | 1/2010 | Krivoruchko et al. |
| 7,985,252 B2 | 7/2011 | Radhakrishnan et al. |
| 7,998,192 B2 | 8/2011 | Atanasoska et al. |
| 8,002,821 B2 | 8/2011 | Stinson |
| 8,048,150 B2 | 11/2011 | Weber et al. |
| 8,052,743 B2 | 11/2011 | Weber et al. |
| 8,052,744 B2 | 11/2011 | Girton |
| 8,052,745 B2 | 11/2011 | Weber |
| 8,057,534 B2 | 11/2011 | Boismier et al. |
| 8,080,055 B2 | 12/2011 | Atanasoska et al. |
| 8,089,029 B2 | 1/2012 | Flanagan |
| 8,128,689 B2 | 3/2012 | Weber et al. |
| 8,236,046 B2 | 8/2012 | Weber |
| 8,585,754 B2 | 11/2013 | Dutta |
| 8,642,068 B2 | 2/2014 | Cottone |
| 8,668,732 B2 | 3/2014 | Scheuermann et al. |
| 8,715,339 B2 | 5/2014 | Atanasoska et al. |
| 8,808,726 B2 | 8/2014 | Atanasoska et al. |
| 8,814,927 B2 | 8/2014 | Shin et al. |
| 8,814,930 B2 | 8/2014 | Zheng et al. |
| 8,834,776 B2 | 9/2014 | Wang et al. |
| 8,840,660 B2 | 9/2014 | Weber |
| 8,876,880 B2 | 11/2014 | Hyodoh et al. |
| 8,876,890 B2 | 11/2014 | Gale et al. |
| 8,888,839 B2 | 11/2014 | Hansen et al. |
| 8,889,823 B2 | 11/2014 | Wang et al. |
| 9,060,892 B2 | 6/2015 | Von Oepen et al. |
| 9,072,820 B2 | 7/2015 | Gale et al. |
| 9,119,905 B2 | 9/2015 | Zheng et al. |
| 9,119,906 B2 | 9/2015 | Tomantschger et al. |
| 2002/0143384 A1 | 10/2002 | Ozasa |
| 2002/0165601 A1 | 11/2002 | Clerc |
| 2003/0040772 A1 | 2/2003 | Hyodoh et al. |
| 2003/0074049 A1 | 4/2003 | Hoganson et al. |
| 2004/0034409 A1 | 2/2004 | Heublein et al. |
| 2006/0155370 A1 | 7/2006 | Brister |
| 2006/0229711 A1 | 10/2006 | Yan et al. |
| 2007/0123973 A1 | 5/2007 | Roth et al. |
| 2008/0069858 A1 | 3/2008 | Weber |
| 2008/0147175 A1 | 6/2008 | Krivoruchko et al. |
| 2008/0221670 A1 | 9/2008 | Clerc et al. |
| 2009/0043330 A1 | 2/2009 | To |
| 2009/0138076 A1 | 5/2009 | Palasis et al. |
| 2009/0187240 A1 | 7/2009 | Clerc et al. |
| 2009/0192588 A1* | 7/2009 | Shin .................. A61F 2/04 623/1.15 |
| 2009/0276036 A1 | 11/2009 | Nagura et al. |
| 2009/0287301 A1 | 11/2009 | Weber |
| 2009/0324684 A1 | 12/2009 | Atanasoska et al. |
| 2010/0030326 A1 | 2/2010 | Radhakrishnan et al. |
| 2010/0076555 A1 | 3/2010 | Marten et al. |
| 2010/0125328 A1 | 5/2010 | Flanagan |
| 2010/0256736 A1 | 10/2010 | Purdy et al. |
| 2010/0280591 A1 | 11/2010 | Shin et al. |
| 2013/0131778 A1 | 5/2013 | Igaki et al. |
| 2013/0138219 A1 | 5/2013 | Toomey et al. |
| 2013/0190676 A1 | 7/2013 | Dickinson et al. |
| 2014/0303714 A1 | 10/2014 | Edwin et al. |

FOREIGN PATENT DOCUMENTS

| | | |
|---|---|---|
| KR | 20120131250 A | 12/2012 |
| WO | 2006081448 A1 | 8/2006 |
| WO | 2008034066 A1 | 3/2008 |
| WO | 2011034768 A1 | 3/2011 |

* cited by examiner

PARTIALLY COATED STENTS

CROSS-REFERENCE TO RELATED APPLICATIONS

This application is a continuation of U.S. application Ser. No. 14/680,593, filed Apr. 7, 2015, which claims the benefit of and priority to U.S. Provisional Application No. 61/976,764, filed Apr. 8, 2014, the entire contents of which are herein incorporated by reference.

TECHNICAL FIELD

The present disclosure pertains to medical devices, systems, and methods for using medical devices. More particularly, the present disclosure pertains to a partially coated stent.

BACKGROUND

Stents are typically tubular endoprostheses used for supporting a diseased or traumatized lumen. For example, stents may be used in body vessels such as in coronary or peripheral vasculature, an esophagus, trachea, bronchi, colon, biliary tract, urinary tract, prostate, brain, or in other bodily locations.

Generally, stents can be permanent or temporary depending on the treatment requirements. Stents may be permanently retained in a patient's body, for example, or for an indeterminate amount of time. Further, some stents are designed to remain in a patient's body temporarily.

After implantation, in some cases, stents migrate from the treatment location, for example, due to exposure to flow of bodily fluids or peristalsis. In order to counteract migration, stents may be partially covered or uncovered, allowing tissue ingrowth into the stent.

As discussed above, on occasion it may be useful to retrieve the stent previously deployed in a body lumen. In covered or partially covered stents, however, tissue ingrowth takes places and hence it becomes challenging to remove the stent from the body.

Therefore, there remains a need for a stent that is less likely to migrate and can also be removed easily, as needed.

SUMMARY

In at least one embodiment, a stent comprises at least one biodegradable filament and a non-biodegradeable coating. The at least one biodegradable filament forms a stent body having a first end portion, a middle portion, and a second end portion opposite the first end portion. The middle portion extends between the first and second end portions. The non-biodegradeable coating encapsulates the at least one biodegradable filament along the middle portion of the stent body. The non-biodegradeable coating forms a barrier such that the non-biodegradeable coating prevents degradation of the at least one biodegradable filament along the middle portion. The first and second end portions are uncoated.

In at least one embodiment, a stent comprises at least one biodegradable monofilament, a non-biodegradeable coating, and at least one retrieval loop. The at least one biodegradable monofilament forms a braided stent body. The braided stent body has a first end portion, a middle portion, and a second end portion opposite the first end portion. The middle portion extends between the first and second end portions. The non-biodegradeable coating encapsulates the at least one biodegradable monofilament along the middle portion of the braided stent body and forms a barrier such that non-biodegradeable coating prevents degradation of at least one biodegradable monofilament along the middle portion. The first and second end portions are uncoated. The retrieval loop is threaded through at least a portion of the middle portion of the braided stent body.

The above summary of some embodiments is not intended to describe each disclosed embodiment or every implementation of the present disclosure. The Figures and Detailed Description, which follow, more particularly exemplify these embodiments.

BRIEF DESCRIPTION OF THE DRAWINGS

A detailed description of the invention is hereafter described with specific reference being made to the drawings.

Figure 1:
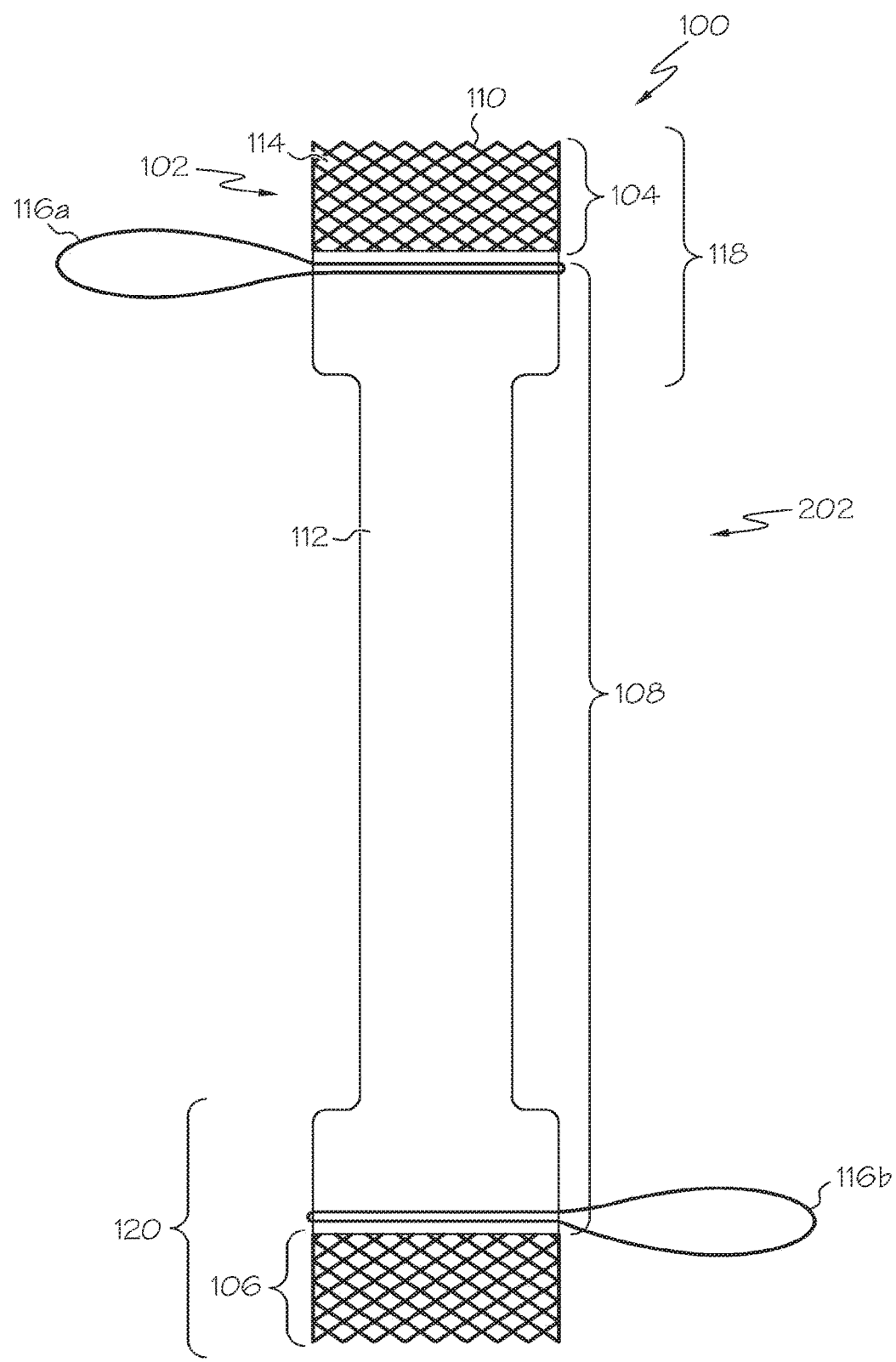
FIG. 1 is a side-view of an embodiment of a stent in an expanded configuration.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

Definitions are provided for the following defined terms. It is intended that these definitions be applied, unless the context indicates otherwise.

The recitation of numerical ranges by endpoints includes all numbers within that range (e.g., 1 to 5 includes 1, 1.5, 2, 2.75, 3, 3.80, 4, and 5).

As used herein, the singular forms "a", "an", and "the" include plural references unless the context clearly indicates otherwise. As used herein, the term "or" is generally employed in its sense including "and/or" unless the context clearly evidences or indicates otherwise.

References herein to "an embodiment," "some embodiments," "other embodiments," etc., indicate that an embodiment includes a particular feature, structure, or characteristic, but not every embodiment necessarily includes the particular feature, structure, or characteristic. Moreover, such phrases do not necessarily refer to the same embodiment. Further, when a particular feature, structure, or characteristic is described in connection with an embodiment (or more embodiments), it should be understood that such feature, structure, or characteristic may also be used in connection with other embodiments, whether or not explicitly described, unless clearly evidenced or stated to the contrary.

The following detailed description should be read with reference to the drawing(s). The drawing(s), which is/are not necessarily to scale, depict one or more illustrative embodiments and is/are not intended to limit the scope of the disclosure.

FIG. 1 is a side-view of a stent 100 that can be implanted in a body lumen (e.g., esophagus, vessel, trachea, bronchi, colon, biliary tract, urinary tract, prostate, brain, duodenum, or other tubular lumen or location) to treat various conditions. As shown, the stent 100 includes a stent body 102 having a first end portion 104, a second end portion 106, and a middle portion 108 extending between the first end portion 104 and the second portion 106. In some embodiments, the stent body 102 has a hollow, tubular structure defining a central lumen through which body fluid, such as mucus or blood, can pass.

Figure 2:
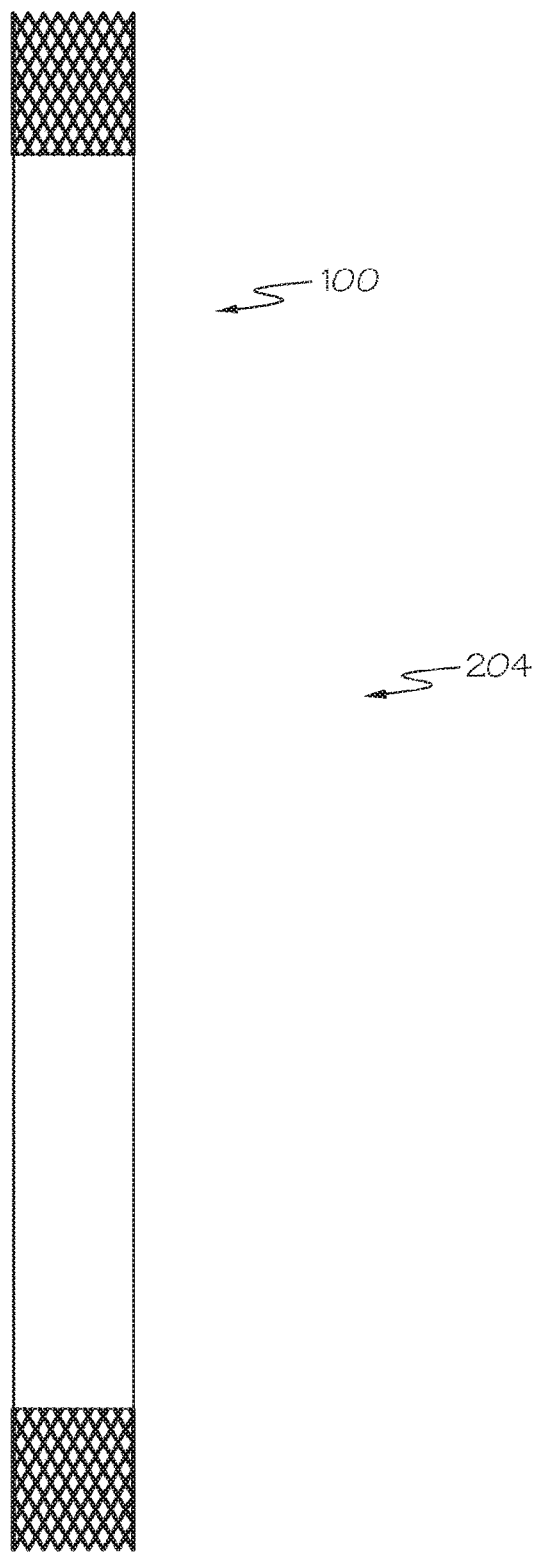
FIG. 2 is a side-view of the embodiment of FIG. 1 in an unexpanded configuration.

The stent 100 has an expanded configuration 202 and an unexpanded configuration 204 (FIG. 2). In the unexpanded configuration 204, the stent 100 has a radially reduced profile; in the expanded configuration 202, the stent 100 has a radially increased profile which can conform to the geometry of a body lumen and, in some embodiments, expand the body lumen. The stent 100 may be delivered to a treatment location through an introducer sheath, endoscope, guide catheter, exterior tube, or via any other suitable delivery device. Further, the stent 100 can be delivered over a guide wire. During delivery, in at least some embodiments, the stent 100 is in the unexpanded configuration 204.

After stent 100 is delivered to the treatment location, the stent 100 may assume the expanded configuration 202 within the body lumen. In some embodiments, in the expanded configuration 202, a cross-sectional area of at least a portion of the stent body 102 (for example, both the first end portion 104 and the second end portion 106) is greater than a cross-sectional area of at least a portion of the middle portion 108. In some embodiments, the cross-sectional area of either the first end portion 104 or the second end portion 106 is greater than at least a portion of the middle portion 108. In some embodiments, one or more of the first end portion 104, the second end portion 106, and the middle portion 108 have varying cross-sectional area. In some embodiments, the stent 100 has one or more flared portions, for example flared ends. In some embodiments, for example as shown in FIG. 1, a first flared portion 118 extends along the entire length of first end portion 104 and along a portion of the middle portion 108. Further, in some embodiments, a second flared portion 120 extends along the entire length of the second end portion 106 and along a portion of the middle portion 108. The one or more flared portions may have an abrupt transition of cross-section or smooth transition.

To deploy the stent 100, a physician may transition the stent 100 between the expanded configuration 202 and the unexpanded configuration 204 using an actuation mechanism, e.g., push-pull mechanism or balloon. In some embodiments, the stent 100 is self-expanding.

In some embodiments, the stent body 102 is formed by braiding one or more biodegradable filaments 110. In some embodiments, the one or more biodegradable filaments 110 have a monofilament structure. Alternatively, in some embodiments, the biodegradable filaments 110 comprise a multi-filament structure. In some embodiments, the biodegradable filaments 110 are braided in a helical pattern, although other arrangements are also suitable. Also, the braiding pattern includes interstices 114 in between the biodegradable filaments 110. The interstices 114 allow tissue ingrowth and thereby prevent or resist migration.

The biodegradable filaments 110 may be formed using a suitable biodegradable material, particularly materials that may be formed into fibers or filaments. Further, in some embodiments, the biodegradable filaments 110 are flexible to allow formation of patterns or braiding, but also have suitable radial strength. Examples of such materials include, for example, poly(lactic-co-glycolic)acid, polyglycolic acid, polylactic acid, or the like. Such materials may degrade, disintegrated, or be absorbed in the body within a few weeks to few months, for example, 3, 4, 5, 6, 10, 12, 18 months.

In some embodiments, the stent 100 includes a non-biodegradeable coating 112 disposed on the filaments 110 of the middle portion 108, encapsulating the biodegradable filaments 110 therealong. In at least some embodiments, the non-biodegradeable coating 112 forms a barrier to prevent the biodegradable filaments 110 from degrading or being absorbed within the body. To this end, the non-biodegradeable coating 112 covers the biodegradable filaments 110 both on an outer surface and inner surface of the stent body 102 such that bodily fluids cannot readily degrade the filaments 110 along the middle portion 108 of the stent body 102

Additionally, in some embodiments, the non-biodegradeable coating 112 is disposed such that the first and second end portions 104, 106 of the stent body 102 remain uncoated. In this way, prior to implantation, the stent 100 is a partially coated stent. As the first end portion 104 and the second end portion 106 remain uncoated, tissue is permitted to ingrow into these portions. The tissue ingrowth secures the stent 100 within the body lumen, preventing migration of the stent 100. Further, the uncoated first and second end portions 104, 106 may biodegrade within the body lumen over a period of time, leaving behind a fully coated stent (e.g., the middle portion 108). Due to the non-biodegradeable coating 112, in some embodiments, the remaining stent 100 (e.g., the middle portion 108) does not have tissue grown into the interstices 114 and, consequently, a physician can retrieve and remove the stent 100 from the body lumen.

Figure 3:
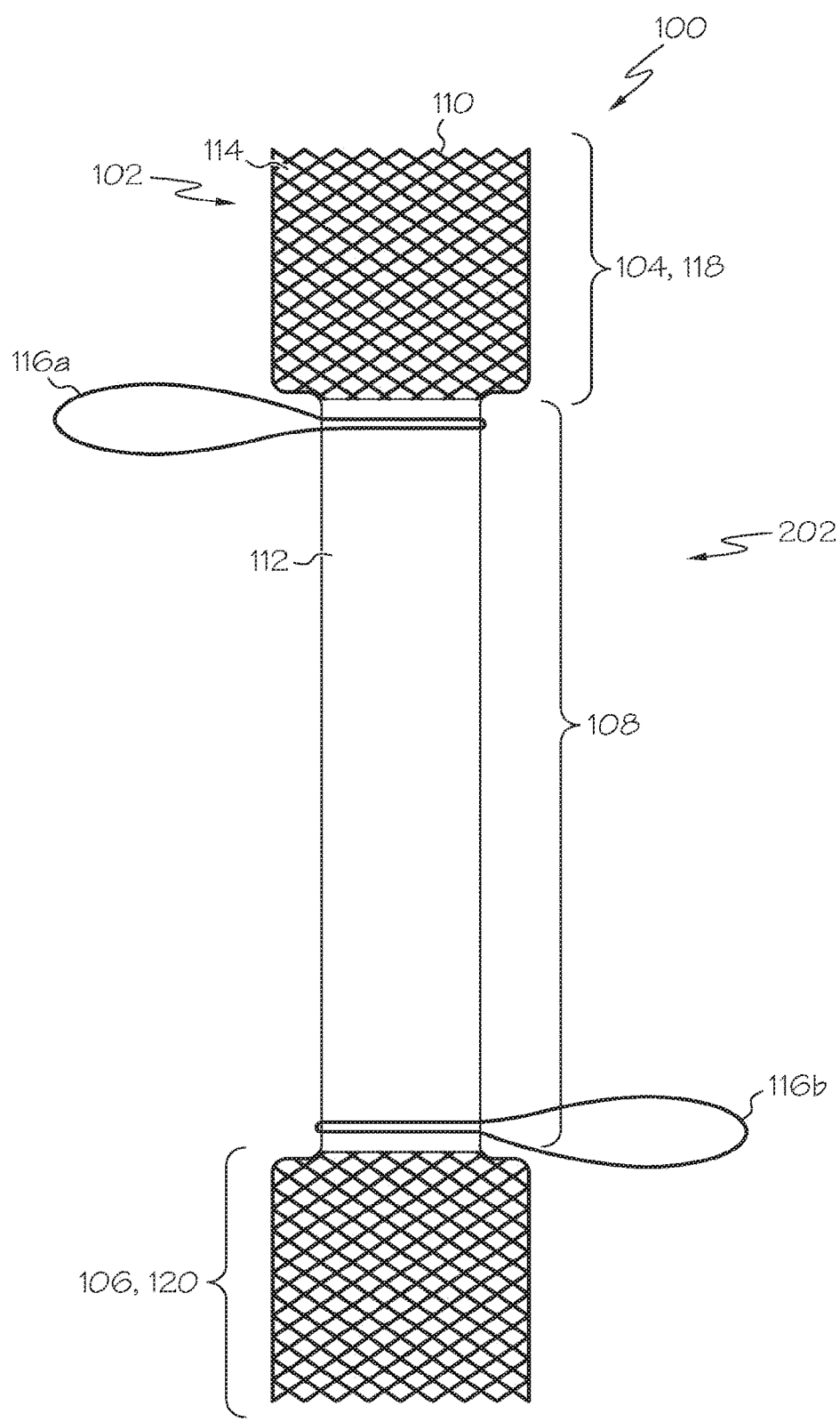
FIG. 3 shows a side-view of an embodiment of a stent in an expanded configuration.

The non-biodegradeable coating 112 can be disposed on the stent 100 in any desirable way. For example, in some embodiments, the entirety of the stent 100 is coated with the non-biodegradeable coating 112 except for the first flared portion 118. Further, in some embodiments, the entirety of the stent 100 is coated with the non-biodegradeable coating 112 except for the second flared portion 120. And, in some embodiments, the entirety of the stent 100 is coated with the non-biodegradeable coating 112 except for the first flared portion 118 and the second flared portion 120, for example as shown in FIG. 3. In such an embodiments, the flared portions 118, 120 degrade, leaving the remaining portion of the stent 100 (e.g., middle portion 108) behind.

The non-biodegradeable coating 112 can be formed using any suitable technique, for example spray coating, dip coating, vapor deposition coating, extrusion, or a combination of these techniques. In some embodiments, the non-biodegradeable coating 112 is applied and secured to the stent body 102 by adhesive bonding, conformal coating, or any suitable combination of these techniques, including a combination of adhesive bonding and conformal coating. In some embodiments, the non-biodegradeable coating 112 is formed from a suitable biocompatible material. In some embodiments, the non-biodegradeable coating 112 is an impermeable material that creates a barrier, preventing bodily fluid from coming into contact with encapsulated biodegradable filament 110, thereby preventing biodegradation of middle portion 108 of the stent 100. In some embodiments, the non-biodegradeable coating 112 not only forms a barrier around the filament but also acts as a covering over the interstices 114, thereby preventing tissue ingrowth and also preventing degradation of the 110 by bodily fluids. In this way, the middle portion 108 of the stent remains intact after degradation of the first and second ends 104, 106 such that it can be removed from the body lumen.

Examples of suitable materials for the non-biodegradeable coating 112 may include, but are not limited to, polyurethane (PU), polyethylene (PE), polytetrafluoroethylene (PTFE), or expanded polytetrafluoroethylene (ePTFE), polyolefins such as high density polyethylene (HDPE) and polypropylene (PP), polyolefin copolymers and terpolymers, polyethylene terephthalate (PET), polyesters, polyamides, polyurethaneureas and polycarbonates, polyvinyl acetate, thermoplastic elastomers including polyether-polyester block copolymers, polyvinyl chloride, polystyrene, polyacrylate, polymethacrylate, polyacrylonitrile, polyacrylamide, silicone resins, combinations and copolymers thereof.

In some embodiments, the stent 100 includes one or more retrieval loops 116a, 116b to facilitate easy retrieval of non-degraded portion of the stent 100. In some embodiments, the retrieval loop(s) are routed through a portion of the middle portion 108 of the stent 100, for example adjacent to the first or second end portion 104, 106. The retrieval loop(s) 116a, 116b may be gripped and pulled to retrieve the stent 100 from the body lumen. The retrieval loop(s) 116a, 116b may be pulled using a device such as, forceps (e.g., rat tooth forceps). Any other suitable retrieval device can also be used.

As shown for example in FIG. 1, the first retrieval loop 116a is longitudinally offset from the second retrieval loop 116b. As a result of having two retrieval loops 116a, 116b, one at or near each end of the degraded stent, the stent 100 can be retrieved from either end.

In some other embodiments, the retrieval loop(s) 116a, 116b are secured to an outer surface of the stent 100 or non-biodegradeable coating 112, for example via an adhesive. In some embodiments, however, one or more retrieval loops 116a, 116b are routed through one or more of the interstices 114. Further, in some embodiments, a portion of the retrieval loop(s) 116a, 116b may be braided into the structure of the stent 100, forming an integral part of the stent structure. In some embodiments, one or more retrieval loop(s) 116a, 116b are formed from a biomaterial. In some embodiments, one or more retrieval loop(s) 116a, 116b are formed from a non-biodegradable material. In some embodiments, one or more retrieval loop(s) 116a, 116b are formed from a shape memory material, such as a shape memory metal, for example a nickel-titanium alloy.

A description of some embodiments of the heat treatments is contained in one or more of the following numbered statements:

Statement 1. A stent comprising:
at least one biodegradable filament forming a stent body, the stent body having a first end portion, a middle portion, and a second end portion opposite the first end portion, the middle portion extending between the first and second end portions; and
a non-biodegradeable coating, the non-biodegradeable coating encapsulating the at least one biodegradable filament along the middle portion of the stent body and forming a barrier such that the non-biodegradeable coating prevents degradation of the at least one biodegradable filament along the middle portion, wherein the first and second end portions are uncoated and biodegradeable.

Statement 2. The stent of statement 1, wherein the at least one biodegradable filament is a monofilament.

Statement 3. The stent of any one of the preceding statements, wherein the stent has an unexpanded configuration and an expanded configuration; in the expanded configuration, at least one of the first end portion and second end portion has a cross-sectional area greater than the cross-sectional area of at least a portion of the middle portion.

Statement 4. The stent of statement 3, wherein, in the expanded configuration, at least a portion of the first end portion and at least a portion of the second end portion has a cross-sectional area greater than at least a portion of the cross-sectional area of the middle portion.

Statement 5. The stent of any one of the preceding statements, wherein the at least one biodegradable filament is formed from poly(lactic-co-glycolic) acid (PLGA), polylactic acid (PLA), polyglycolic acid (PGA), poly(ortho ester) (POE), poly(epsilon-caprolactone) (PCL), and polyhydroxybutyrate-valerate (PHBV), or polydioxanone (PDO).

Statement 6. The stent of any one of the preceding statements, wherein the non-biodegradeable coating is formed from a silicone polymer, silicone copolymer, polyurethane, polystyrene-polyethylene/butylene-polystyrene (SEBS) copolymer, acrylate polymer, acrylate copolymer, methacrylate polymer, methacrylate copolymer, fluorinated polymer, (modified) ethylene-tetrafluoroethylene copolymer (ETFE) polymer, polytetrafluoroethylene (PTFE), poly(tetrafluoroethylene-co-hexafluoropropene) (FEP), polyvinylidene fluoride (PVDF), and combinations thereof.

Statement 7. The stent of any one of the preceding statements further comprising at least one retrieval loop.

Statement 8. The stent of statement 7, wherein at least a portion of the retrieval loop is routed through at least a portion of the middle portion.

Statement 9. The stent of statement 7 further comprising a plurality of retrieval loops.

Statement 10. The stent of statement 9, wherein the plurality of retrieval loops comprises a first retrieval loop and a second retrieval loop, the second retrieval loop threaded through at least a portion of the middle portion, the second retrieval loop being longitudinally offset from the first retrieval loop.

Statement 11. The stent of statement 7, 8, 9, or 10 wherein the at least one retrieval loop is formed from a shape memory material.

Statement 12. The stent of statement 11, wherein the shape memory material is a nickel-titanium alloy.

Statement 13. The stent of any one of the preceding statements further being an esophageal stent.

Statement 14. The stent of any one of the preceding statements, wherein the at least one biodegradable filament is braided to form the stent body.

Statement 15. The stent of any one of the preceding statements, wherein the stent body defines a plurality of interstices, the interstices being covered by the non-biodegradeable coating along the middle portion of the stent body, thereby preventing tissue ingrowth therealong.

Statement 16. The stent of any of the preceding statements, wherein the stent body comprises a first flared portion, a portion of the first flared portion being coated with the non-biodegradeable coating and a portion of the flared portion being uncoated.

Statement 17. The stent of statement 16, wherein the stent body comprises a second flared portion, a portion of the second flared portion being coated with the non-biodegradeable coating and a portion of the second flared portion being uncoated.

Statement 18. The stent of statement 16, wherein the first and second flared portions are uncoated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of treating a body lumen comprising:
   implanting a stent in the body lumen, the stent including:
   at least one biodegradable filament forming a stent body with a plurality of interstices, the stent body having a first end portion, a middle portion, and a second end portion opposite the first end portion, the middle portion extending between the first and second end portions; and
   a non-biodegradeable coating, the non-biodegradeable coating encapsulating the at least one biodegradable filament along the middle portion of the stent body and forming a barrier such that the non-biodegradeable coating prevents degradation of the at least one biodegradable filament along the middle portion, wherein the first and second end portions are uncoated and biodegradeable;
   allowing tissue ingrowth into the interstices in the first and second end portions;
   allowing the at least one biodegradable filament forming the first and second end portions to biodegrade; and
   thereafter, removing the middle portion of the stent from the body lumen.

2. The method of claim 1, wherein removing the middle portion of the stent includes removing both the at least one biodegradable filament forming the middle portion, and the non-biodegradeable coating.

3. The method of claim 1, wherein the non-biodegradeable coating is an impermeable material that prevents biodegradation of and tissue ingrowth through the middle portion.

4. The method of claim 1, wherein the stent further includes at least one retrieval loop attached to the middle portion, wherein removing the middle portion of the stent includes grasping and pulling the at least one retrieval loop.

5. The method of claim 4, wherein the at least one retrieval loop is attached to the non-biodegradeable coating.

6. The method of claim 4, wherein the at least one retrieval loop is attached to the at least one biodegradable filament.

7. The method of claim 4, wherein the stent includes two retrieval loops spaced apart longitudinally along the middle portion, wherein removing the middle portion of the stent includes grasping a single retrieval loop that is positioned most proximal.

8. The method of claim 4, wherein the at least one retrieval loop is formed from a non-biodegradable material.

9. The method of claim 1, wherein implanting the stent in the body lumen includes implanting the stent in a patient's esophagus.

10. A method of treating a body lumen comprising:
    implanting a stent in the body lumen, the stent including:
    at least one biodegradable filament forming a stent body with a plurality of interstices, the stent body having a first end portion, a middle portion, and a second end portion opposite the first end portion, the middle portion extending between the first and second end portions; and
    a non-biodegradeable coating, the non-biodegradeable coating encapsulating the at least one biodegradable filament along at least the middle portion of the stent body and forming a coated region with a barrier such that the non-biodegradeable coating prevents degradation of the at least one biodegradable filament along the coated region, wherein at least one of the first and second end portions is uncoated and biodegradeable, defining one or more uncoated end portions;
    allowing tissue ingrowth into the interstices in the one or more uncoated end portions;
    allowing the at least one biodegradable filament forming the one or more uncoated end portions to biodegrade; and
    thereafter, removing the coated region of the stent from the body lumen.

11. The method of claim 10, wherein the coated region includes the middle portion and the first end portion, wherein allowing tissue ingrowth includes allowing tissue ingrowth into the interstices in the second end portion, allowing the at least one biodegradable filament forming the one or more uncoated end portions to biodegrade includes allowing the at least one biodegradable filament forming the second end portion to biodegrade, and removing the coated region includes removing the middle portion and the first end portion.

12. The method of claim 10, wherein removing the coated region of the stent includes removing both the at least one biodegradable filament and the non-biodegradeable coating forming the coated region.

13. The method of claim 10, wherein the non-biodegradeable coating is an impermeable material that prevents biodegradation of and tissue ingrowth through the coated region.

14. The method of claim 10, wherein the stent further includes at least one retrieval loop attached to the middle portion, wherein removing the coated region of the stent includes grasping and pulling the at least one retrieval loop.

15. The method of claim 14, wherein the at least one retrieval loop is attached to the non-biodegradeable coating.

16. The method of claim 14, wherein the at least one retrieval loop is attached to the at least one biodegradable filament.

17. The method of claim 14, wherein the stent includes two retrieval loops spaced apart longitudinally along the middle portion, wherein removing the coated region of the stent includes grasping a single retrieval loop that is positioned most proximal.

18. The method of claim 14, wherein the at least one retrieval loop is formed from a non-biodegradable material.

19. The method of claim 10, wherein implanting the stent in the body lumen includes implanting the stent in a patient's esophagus.

20. The method of claim 10, wherein the stent has an unexpanded configuration and an expanded configuration, and in the expanded configuration, at least one of the first end portion and second end portion has a cross-sectional area greater than the cross-sectional area of at least a portion of the middle portion.

* * * * *